United States Patent
Fujiki et al.

[11] Patent Number: 5,173,529
[45] Date of Patent: Dec. 22, 1992

[54] ADHESIVE ORGANOPOLYSILOXANE COMPOSITION

[75] Inventors: Hironao Fujiki, Takasaki; Toshiaki Takahashi, Annaka, both of Japan

[73] Assignee: Shin-Etsu Chemical Co., Ltd., Tokyo, Japan

[21] Appl. No.: 702,061

[22] Filed: May 17, 1991

[30] Foreign Application Priority Data

May 30, 1990 [JP] Japan .................. 2-138607

[51] Int. Cl.$^5$ ............................................. C08K 5/54
[52] U.S. Cl. ................................. 524/188; 524/730; 524/731; 428/447; 528/15
[58] Field of Search .................. 528/15; 524/188, 730, 524/731; 428/447

[56] References Cited

U.S. PATENT DOCUMENTS 4,257,936  3/1981  Matsumoto et al. ............. 528/15
4,943,601  7/1990  Dinallo, Sr. ..................... 524/731

Primary Examiner—Melvyn I. Marquis
Attorney, Agent, or Firm—Wyatt, Gerber, Burke & Badie

[57] ABSTRACT

An organopolysiloxane-based adhesive composition is proposed which exhibits very reliable adhesive bonding by being cured not only at an elevated temperature but also at room temperature. The adhesive composition comprises, in addition to an alkenyl group-containing diorganopolysiloxane, an organohydrogenpolysiloxane, which serves as a crosslinking agent of the alkenyl group-containing diorganopolysiloxane by the hydrosilation reaction, and a platinum compound to catalytically promote the reaction, a compound having an α-substituted or unsubstituted β-aminopropionyl group and an alkoxysilyl-substituted alkyl group such as the compounds of the formulas $(CH_3O)_3Si-(CH_2)_3-NH-(CH_2)_2-CO-O-(CH_2)_3-Si(OCH_3)_3$;

$C_6H_5-CH_2-NH-(CH_2)_2-CO-O-(CH_2)_3-Si(OCH_3)_3$;

$CH_2=CH-CH_2-NH-(CH_2)_2-CO-O-(CH_2)_3-Si(OCH_3)_3$;

and $(CH_3O)_3Si-(CH_2)_3-NH-(CH_2)_2-CO-O-CH_2-CH=CH_2$.

9 Claims, No Drawings

ADHESIVE ORGANOPOLYSILOXANE COMPOSITION

BACKGROUND OF THE INVENTION

The present invention relates to a novel adhesive organopolysiloxane composition or, more particularly, to an organopolysiloxane-based adhesive composition capable of exhibiting excellent adhesive bonding strength on various kinds of substrate materials including metals, plastics, ceramics and the like even without a pretreatment of the substrate surface with a primer composition or even at room temperature so as to be useful in various industrial fields such as electric, electronic and architectural industries.

Among the various types of adhesive compositions used for adhesive bonding of parts in electric and electronic industries or as a sealing material of buildings in architectural works including polyurethane-based, acrylic resin-based, epoxy resin-based and silicone-based ones, the silicone- or organopolysiloxane-based adhesive compositions are widely used as a high-grade adhesive in view of the outstandingly superior performance in respects of their excellent heat resistance, weatherability and electric properties as well as rapid relaxation of the stress produced by heating and cooling.

Silicone-based adhesive compositions are usually formulated with an adhesion-improver for which many proposals and attempts have been made heretofore. For example, Japanese Patent Kokai 48-16952 proposes use of an organopolysiloxane having at least one hydrogen atom directly bonded to the silicon atom and at least one trialkoxysilyl group simultaneously in a molecule as the adhesion-improver. Japanese Patent Kokai 50-39345 proposes use of an organopolysiloxane having at least one hydrogen atom directly bonded to the silicon atom and at least one ester group and/or glycidyl group simultaneously in a molecule as the adhesion-improver. Further, Japanese Patent Publications 52-8854 and 55-41702 disclose a reaction product of an aminoalkyl alkoxy silane and a glycidyloxyalkyl alkoxy silane as the adhesion-improver of a silicone-based adhesive composition.

The silicone-based adhesive compositions in the prior art admixed with the above mentioned adhesion-improvers, however, are not quite satisfactory. In recent years, moreover, various kinds of materials having little susceptibility to adhesive bonding have come to prevailing use in various industrial fields so that these prior art adhesive compositions can no longer comply with the demand for effectively bonding these hardly bondable materials. Another problem in these prior art adhesive compositions consists, while the adhesive composition must be stored in two packages for different ingredients since a ready-mixed adhesive composition has a limited pot life, in the storage stability of some ingredients of the composition resulting in the loss of the adhesive bonding power, in particular, when such an ingredient is compounded after a prolonged storage at room temperature or an elevated temperature. Moreover, some of the silicone-based adhesive compositions cannot exhibit full adhesive bonding strength when the bonding work therewith is undertaken at room temperature so that the application of the adhesive composition to the use as a sealing material of buildings are greatly limited.

Japanese Patent Publications 52-8854 and 55-41702 teach that the adhesive bonding strength by using a hydrosilationcurable silicone-based adhesive composition can be improved by admixing the adhesive with an adhesion improver which is, for example, an organosilicon compound expressed by the structural formula

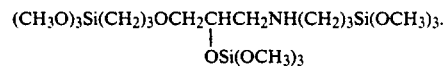

This adhesive composition, however, is not quite satisfactory becaause improvement in the adhesive bonding strength therewith can be obtained only when it is cured at a relatively high temperature.

SUMMARY OF THE INVENTION

The present invention accordingly has an object to provide a novel and improved organopolysiloxane-based adhesive composition free from the above described problems and disadvantages in the silicone-based adhesive compositions in the prior art.

Thus, the organopolysiloxane-based adhesive composition of the present invention comprises, as a mixture:

(a) 100 parts by weight of a diorganopolysiloxane having, in a molecule, at least two alkenyl groups bonded to the silicon atoms;

(b) an organohydrogenpolysiloxane having, in a molecule, at least three on an average of hydrogen atoms directly bonded to the silicon atoms in such an amount that from 0.5 to 10 moles of the silicon-bonded hydrogen atoms are provided per mole of the alkenyl groups in the component (a);

(c) from 0.01 to 10 parts by weight of a β-aminopropionyl group-containing compound represented by the general formula

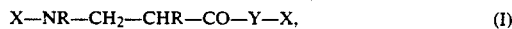

in which each R is, independently from the other a hydrogen atom or a monovalent hydrocarbon group having 1 to 10 carbon atoms, Y is an oxygen atom or NR and each X is, independently from the other, a monovalent hydrocarbon group having 1 to 10 carbon atoms or an organosilyl-substituted monovalent hydrocarbon group of the formula Z₃SiQ, Z being, each independently from the others, a monovalent hydrocarbon group or an alkoxy group having 1 to 8 carbon atoms and Q being a divalent hydrocarbon group containing one or a plurality of methylene groups —CH₂— of which one is unreplaced or replaced with an imino group —NH—, with the proviso that at least either one of the two X groups is an organosilyl-substituted monovalent hydrocarbon group of the formula Z₃SiQ of which at least one of the three Z groups is an alkoxy group or an alkoxy-substituted alkoxy group; and (d) a compound of a platinum-group metal in a catalytic amount.

DETAILED DESCRIPTION OF THE PREFERRED EMBODIMENTS

As is described above, the essential ingredients in the organopolysiloxane-based adhesive composition of the invention include the components (a) to (d), of which the components (a), (b) and (d) are rather conventional. Namely, curing of the composition is effected by the addition reaction or so-called hydrosilation reaction between the alkenyl groups in the component (a) and the silicon-bonded hydrogen atoms in the component (b) while this reaction is promoted by the component (d) which is a compound of a platinum group metal as the catalyst. The most characteristic feature of the inventive composition is admixture of a unique compound as the component (c) represented by the general formula (I), by virtue of which the composition is imparted with good curability even at a relatively low temperature of 80° C. or below or even at room temperature to exhibit excellent adhesive bonding strength to the substrate surface on which the composition has been cured in contact. The adhesive bonding strength obtained by the inventive adhesive composition is very strong and not limited by the kind of the substrate materials including polycarbonate resins hardly susceptible to adhesive bonding with prior art adhesive compositions so that the inventive adhesive composition is useful in the manufacture of electric and electronic devices and instruments and in building works not only as an adhesive but also as a sealing, coating or potting material.

The component (a) as the base ingredient of the inventive adhesive composition is a diorganopolysiloxane having, in a molecule, at least two alkenyl groups of, for example 2 to 6 carbon atoms such as vinyl, allyl, 1-butenyl and 1-hexenyl groups, of which vinyl group is preferred in view of the relatively simple synthetic procedure for the preparation of the diorganopolysiloxane having vinyl groups. The organic groups other than the alkenyl groups bonded to the silicon atoms in the diorganopolysiloxane are each a monovalent hydrocarbon group having 1 to 10 or, preferably, 1 to 8 carbon atoms including alkyl groups, e.g., methyl, ethyl, propyl, butyl and octyl groups, aryl groups, e.g., phenyl, tolyl and naphthyl groups and aralkyl groups, e.g., 2-phenylethyl and 2-phenylpropyl groups. These hydrocarbon groups can be substituted for a part or all of the hydrogen atoms therein by halogen atoms, cyano groups and the like as in chloromethyl, 2-cyanoethyl and 3,3,3-trifluoropropyl groups. It is preferable that all or at least 50% of the organic groups other than alkenyl in the diorganopolysiloxane are methyl groups since vinyl-containing dimethylpolysiloxanes can exhibit good mechanical properties after curing even when the degree of polymerization or viscosity thereof before curing is relatively low in addition to the economical advantage due to the relatively low costs for the preparation thereof.

Although a small amount of branches in the molecular structure may have no particular adverse influences, the diorganopolysiloxane as the component (a) should desirably have a straightly linear molecular structure. The average degree of polymerization of the diorganopolysiloxane should be such that the viscosity thereof at 25° C. is in the range from 50 to 300,000 centipoise or, preferably, from 100 to 30,000 centipoise. When the viscosity thereof is too low, the composition after curing may be poor in respect of the mechanical properties such as elongation and rubbery elasticity. When the viscosity thereof is too high, on the other hand, certain inconveniences are caused relative to the workability of the composition in casting, potting, coating, impregnation and the like.

The organohydrogenpolysiloxane as the component (b) in the inventive adhesive composition serves as a cross-linking agent of the above described alkenyl-containing diorganopolysiloxane as the component (a) to effect curing of the composition by the addition reaction or hydrosilation reaction between the alkenyl groups in the component (a) and the hydrogen atoms directly bonded to the silicon atoms in the component (b). In this regard, the organohydrogen-polysiloxane should have, in a molecule, at least two or, preferably, at least three hydrogen atoms directly bonded to the silicon atoms, i.e. silicon-bonded hydrogen atoms. The molecular structure of the organohydrogenpolysiloxane is not particularly limitative including, straightly linear, branched, three-dimensional and cyclic structures. The organic groups bonded to the silicon atoms in the organohydrogenpolysiloxane are unsubstituted or substituted monovalent hydrocarbon groups including those groups given as the examples of the organic groups in the component (a) excepting alkenyl groups. Preferably, the organic groups are methyl groups.

The degree of polymerization or viscosity of the organohydrogenpolysiloxane is not particularly limitative although those having a too low viscosity have volatility to cause a loss by evaporation and those having a too high viscosity would be expensive due to the difficulty in the synthetic preparation resulting in high costs. In this regard, the viscosity thereof is practically limited not to exceed 10,000 centipoise or, mostly, in the range from 0.9 to 10,000 centipoise at 25° C.

The amount of the organohydrogenpolysiloxane as the component (b) in the inventive adhesive composition should be sufficient to provide from 0.5 to 10 moles of the silicon-bonded hydrogen atoms therein per mole of the alkenyl groups in the component (a). When the amount thereof is too small, the crosslinking density in the composition after curing would be too low so that the cured composition would not have good mechanical properties. When the amount thereof is too large, on the other hand, foaming of the composition may take place in the course of curing in addition to the disadvantageous influences on the mechanical properties of the cured composition, in particular, at elevated temperatures.

The component (c), which is the most characteristic ingredient in the inventive composition, is a β-aminopropionyl group-containing compound disclosed in U.S. Pat. No. 4,374,237 and serves as an adhesion improver. It is an α-substituted or unsubstituted, β-aminopropionyl group containing compound represented by the general formula $$X-NR-CH_2-CHR-CO-Y-X, \qquad (I)$$

in which each R is, independently from the other, a hydrogen atom or a monovalent hydrocarbon group having 1 to 10 carbon atoms, Y is an oxygen atom or NR and each X is, independently from the other, a monovalent hydrocarbon group having 1 to 10 carbon atoms or an organosilyl-substituted monovalent hydrocarbon group of the formula $Z_3SiQ$, Z being, each independently from the others, a monovalent hydrocarbon group, an alkoxy group or an alkoxy-substituted alkoxy group having 1 to 8 carbon atoms and Q being a divalent hydrocarbon group containing one or a plurality of methylene groups $-CH_2-$ of which one is unreplaced or replaced with an imino group $-NH-$, with the proviso that at least either one of the two X groups is an organosilyl-substituted monovalent hydrocarbon group of the formula $Z_3SiQ$ of which at least one of the three Z groups is an alkoxy group or an alkoxy-substituted alkoxy group.

The monovalent hydrocarbon group having 1 to 10 carbon atoms denoted by R in the formula (I) includes unsubstituted or substituted monovalent hydrocarbon groups exemplified by alkyl groups, e.g., methyl, ethyl, propyl and butyl groups, alkenyl groups, e.g., vinyl and allyl groups, and aryl groups, e.g., phenyl and tolyl groups, as well as halogen- or cyano-substituted groups, e.g., chloromethyl, 2-cyanoethyl and 3,3,3-trifluoropropyl groups.

The symbol X in the formula (I) denotes either a monovalent hydrocarbon group exemplified by those given as the examples of the group denoted by R or an organosilyl-substituted monovalent hydrocarbon group $Z_3SiQ$, in which each Z is a monovalent hydrocarbon group having 1 to 8 carbon atoms, which can be selected from the same groups given as the examples of the group denoted by R, or an alkoxy or alkoxy-substituted alkoxy group, such as methoxy, ethoxy, propoxy, butoxy, methoxyethoxy and ethoxyethoxy groups, and Q denotes a divalent hydrocarbon group having 1 to 8 or, preferably, 2 to 6 carbon atoms containing one or a plurality of methylene groups —$CH_2$— of which one is unreplaced or replaced with an imino group —NH—, such as ethylene, propylene and phenylene groups. At least one of the three groups denoted by Z in $Z_3SiQ$ is an alkoxy or alkoxy-substituted alkoxy group.

The symbol Y in the formula (I) is a divalent group linking the carbonyl group CO and one of the groups denoted by X and can be an oxygen atom or an unsubstituted or substituted imino group of the formula NR, R having the same meaning as defined above.

Examples of the β-aminopropionyl-containing compound suitable as the component (c) include those expressed by the structural formulas of:

(MeO)$_3$Si—(CH$_2$)$_3$—NH—CH$_2$—CH$_2$—CO—O—(CH$_2$)$_3$—Si(OMe)$_3$;

Ph—CH$_2$—NH—CH$_2$—CH$_2$—CO—O—(CH$_2$)$_3$—Si(OMe)$_3$;

CH$_2$=CH—CH$_2$—NH—CH$_2$—CH$_2$—CO—O—(CH$_2$)$_3$—Si(OMe)$_3$;

and (MeO)$_3$Si—(CH$_2$)$_3$—NH—CH$_2$—CH$_2$—CO—O—CH$_2$—CH=CH$_2$, in which Me and Ph denote a methyl group and a phenyl group, respectively.

These compounds can be prepared by the so-called Michael addition reaction between an amine compound having an active hydrogen atom represented by the formula X—NR—H and an α-substituted or unsubstituted acryloyl compound of the formula CH$_2$=CR—CO—Y—X, in which each symbol has the same meaning as defined above. The group denoted by X in at least either one of the two reactants is the group denoted by $Z_3SiQ$. Examples of the amine compound include: ethylamine, diethylamine, propylamine, dipropylamine, diallylamine, octylamine, ethylenediamine, hexamethylenediamine, triethylenetetramine, aniline, benzylamine and the like as well as amino-containing organosilicon compound of the formula $Z_3Si$—Q—NR—H, in which each symbol has the same meaning as defined above. Examples of the amine compound include the compounds expressed by the following formulas:

(EtO)$_3$Si—(CH$_2$)$_3$—NH$_2$;

(EtO)$_2$MeSi—(CH$_2$)$_3$—NH$_2$;

(MeO)$_3$Si—(CH$_2$)$_3$—NH$_2$;

(EtO)$_3$Si—(CH$_2$)$_3$—NH—(CH$_2$)$_2$—NH$_2$;

(MeO)$_3$Si—(CH$_2$)$_3$—NH—(CH$_2$)$_2$—NH$_2$;

(MeO)$_2$MeSi—(CH$_2$)$_3$—NH—(CH$_2$)$_2$—NH$_2$;

(MeOCH$_2$CH$_2$O)$_3$Si—(CH$_2$)$_3$—NH$_2$;

(MeO)$_3$Si—(CH$_2$)$_3$—O—CH$_2$—CHMe—CH$_2$—NH$_2$;

(MeO)$_3$Si—CH=CH—CMe$_2$—O—(CH$_2$)$_3$—NH$_2$;

(MeO)$_3$Si—(CH$_2$)$_3$—NH—(CH$_2$)$_2$—NH—Et;

(MeO)$_3$Si—CH=CH—CMe$_2$—O—(CH$_2$)$_3$—NH—(CH$_2$)$_3$—NH$_2$;

(MeO)$_3$Si—(CH$_2$)$_3$—NH—Ph;

(MeO)$_3$Si—(CH$_2$)$_3$—NH—(CH$_2$)$_2$—NH—CH$_2$—CH=CH$_2$;

and (MeO)$_3$Si—(CH$_2$)$_3$—NH—CH$_2$—CH=CH$_2$, in which Me, Et and Ph denote methyl, ethyl and phenyl groups, respectively. Among the above named amine compounds, those having two or more of nitrogren atoms are less preferable in view of the possible toxicity against the catalyst as the component (d) described below.

Examples of the acryloyl-containing compound to be reacted with the above described amine compound by the Michael reaction include: esters of (meth)acrylic acid, i.e. acrylic or methacrylic acid, with a monohydric alcohol such as methyl (meth)acrylate, ethyl (meth)acrylate, butyl (meth)acrylate, vinyl (meth)acrylate, allyl (meth)acrylate, benzyl (meth)acrylate, glycidyloxypropyl (meth)acrylate and the like, esters of (meth)acrylic acid with a dihydric alcohol and esters of (meth)acrylic acid with a trihydric alcohol, e.g., glycerin, as well as esters or amides of (meth)acrylic acid with an alkoxysilyl-substituted monohydric alcohol or amine of the general formula CH$_2$=CR—CO—Y—QSiZ$_3$ such as those expressed by the formulas of:

CH$_2$=CR—CO—O—CH$_2$—Si(OMe)$_3$;

CH$_2$=CR—CO—O—(CH$_2$)$_3$—Si(OMe)$_3$;

CH$_2$=CR—CO—O—CH$_2$—Si(OEt)$_3$;

CH$_2$=CR—CO—O—(CH$_2$)$_3$—Si(OEt)$_3$;

CH$_2$=CR—CO—O—(CH$_2$)$_3$—Si(O—C$_2$H$_4$—O—Me)$_3$;

CH$_2$=CR—CO—O—(CH$_2$)$_3$—SiMe(OMe)$_2$;

CH$_2$=CR—CO—O—(CH$_2$)$_3$—SiVi(OMe)$_2$;

and

CH$_2$=CR—CO—NH—(CH$_2$)$_3$—Si(OMe)$_3$, in which R has the same meaning as defined above and Me, Et and Vi denote methyl, ethyl and vinyl groups, respectively.

It is essential that at least either one of the amine compound and the acryloyl-containing compound is one of the above given classes of organosilicon compounds in order that at least either one of the two X groups in the general formula (I) is an organosilyl-substituted monovalent hydrocarbon group of the formula $Z_3SiQ$.

The Michael reaction between the above described amine compound and (meth)acryloyl compound can proceed even at room temperature by merely blending the reactants although it is preferable that the reaction mixture is heated when the amine compound is a secondary amine compound or the (meth)acryloyl compound is a methacryloyl compound. When the reaction is performed under heating, the reaction mixture is desirably admixed with a polymerization inhibitor in order to prevent polymerization of the (meth)acryloyl compound.

The amount of the component (c) in the inventive composition is in the range from 0.01 to 10 parts by weight or, preferably, from 0.2 to 3 parts by weight per 100 parts by weight of the alkenyl-containing diorganopolysiloxane as the component (a). When the amount thereof is too small, full improvement in the adhesive bonding strength cannot be obtained. When the amount thereof is too large, on the other hand, certain adverse influences are caused on the physical properties of the composition after curing also resulting in a decreased adhesive bonding strength.

The component (d) in the inventive composition serves as a catalyst to promote the addition reaction or hydrosilation reaction between the alkenyl groups in the component (a) and the silicon-bonded hydrogen atoms in the component (b). Platinum group metals, i.e. platinum, palladium and rhodium, or compounds of these metals, of which platinum compounds are preferred, are known to have the catalytic activity. Examples of suitable platinum catalysts include chloroplatinic acid, alcohol-modified chloroplatinic acid and complexes of chloroplatinic acid with an olefin, ketone or vinyl siloxane as well as platinum compounds supported by a catalyst carrier such as silica, alumina and the like and platinum black. Examples of the palladium catalysts include tetrakis(triphenyl phosphine) palladium and a mixture of palladium black with triphenyl phosphine. Examples of the rhodium catalysts include tetrakis(triphenyl phosphine) rhodium and a mixture of rhodium black with triphenyl phosphine. Although the amount of these catalytic compounds in the inventive composition is a catalytic amount depending on the desired velocity of curing, it is usual that the amount is in the range from 0.1 to 1000 ppm by weight or, preferably, from 0.3 to 200 ppm by weight calculated as metal relative to the total amount of the components (a) and (b). When the amount of the component (d) is too small, the curing reaction cannot proceed at a velocity as desired as a matter of course. Increase of the amount of the component (d) over the above mentioned upper limit has no particular additional advantages rather with an economical disadvantage due to the expensiveness of the compounds of platinum group metals in general.

The organopolysiloxane-based adhesive composition of the present invention can be prepared by uniformly blending the above described essential constituents by using a known blending machine although the composition can optionally be admixed with various kinds of additives conventionally used in silicone-based adhesive compositions according to need. Examples of such optional additives include fillers such as finely divided fumed and precipitated silica fillers, quartz powder, diatomaceous earth, titanium dioxide, aluminum oxide, zinc oxide, iron oxide, mica, clay, carbon black, graphite powder, glass beads, metal powders, calcium carbonate and the like, heat-resistance improvers such as ceric hydroxide and the like, flame-retardant agents, pigments, tackifiers, anti-fungal agents, organic solvents such as toluene, hexane and the like as well as dimethylpolysiloxanes of low molecular weight as a viscosity-controlling agent.

The adhesive composition prepared in the above described manner can be applied to the surface of any material used in electric or electronic devices and instruments or in buildings and cured thereon even at room temperature or by heating at a relatively low temperature of 80° C. or below to exhibit excellent adhesive bonding strength.

In the following, the organopolysiloxane-based adhesive composition of the present invention is illustrated in more detail by way of examples and comparative examples as preceded by the description of the synthetic procedure for the preparation of the β-aminopropionyl-containing compounds used as the component (c). The term of "parts" in the following description always refers to "parts by weight". The adhesive compositions prepared in the examples and comparative examples were tested for the shearing adhesive bonding strength according to the procedure specified in JIS K 6850.

SYNTHETIC PREPARATION 1

Into a flask of 300 ml capacity equipped with a stirrer and a thermometer were introduced 117.2 g (0.50 mole) of 3-acryloxypropyl trimethoxy silane and 95.0 g (0.53 mole) of 3-aminopropyl trimethoxy silane and the mixture was agitated for 30 minutes at room temperature and then for 24 hours at 60° to 70° C. under a stream of dry nitrogen gas to effect the reaction therebetween. When the gas chromatographic analysis indicated complete disappearance of the 3-acryloxypropyl trimethoxy silane in the reaction mixture, the reaction mixture was subjected to stripping at 80° to 90° C. under a reduced pressure of 5 mmHg and freed from any trace amount of volatile impurities such as methyl alcohol and the unreacted 3-aminopropyl trimethoxy silane to give 203.9 g of a liquid product, referred to as C-I hereinbelow, which could be identified by the infrared absorption spectrophotometric, NMR spectrometric and mass spectrometric analyses to be a compound expressed by the structural formula

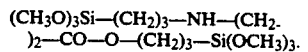

$(CH_3O)_3Si-(CH_2)_3-NH-(CH_2)_2-CO-O-(CH_2)_3-Si(OCH_3)_3$.

The above mentioned yield of the product corresponds to 96% of the theoretical value.

SYNTHETIC PREPARATION 2

Into a flask of 300 ml capacity equipped with a stirrer and a thermometer were introduced 140.6 g (0.60 mole) of 3-acryloxypropyl trimethoxy silane and 67.5 g (0.63 mole) of benzylamine and the mixture was agitated for 30 minutes at room temperature and then for 24 hours at 80° to 90° C. under a stream of dry nitrogen gas to effect the reaction. When the gas chromatographic analysis indicated complete disappearance of the 3-acryloxypropyl trimethoxy silane in the reaction mixture, the reaction mixture was subjected to stripping at 70° to 80° C. under a reduced pressure of 5 mmHg and freed from any trace amount of volatile impurities and and freed from any trace amount of volatile impurities and the unreacted benzylamine to give 195.7 g of a liquid product, referred to as C-II hereinbelow, which could be identified by the infrared absorption spectrophotometric, NMR spectrometric and mass spectrometric analyses to be a compound expressed by the structural formula

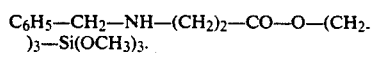

C$_6$H$_5$—CH$_2$—NH—(CH$_2$)$_2$—CO—O—(CH$_2$)$_3$—Si(OCH$_3$)$_3$.

The above mentioned yield of the product corresponds to 94% of the theoretical value.

SYNTHETIC PREPARATION 3

A compound, referred to as C-III hereinbelow, expressed by the structural formula

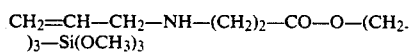

CH$_2$=CH—CH$_2$—NH—(CH$_2$)$_2$—CO—O—(CH$_2$)$_3$—Si(OCH$_3$)$_3$ was prepared in substantially the same synthetic procedure as in Synthetic Preparation 1 described above excepting replacement of 95.0 g of the 3-aminopropyl trimethoxy silane with 30.3 g (0.53 mole) of allylamine.

SYNTHETIC PREPARATION 4

A compound, referred to as C-IV hereinbelow, expressed by the structural formula

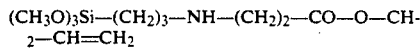

(CH$_3$O)$_3$Si—(CH$_2$)$_3$—NH—(CH$_2$)$_2$—CO—O—CH$_2$—CH=CH$_2$ was prepared in substantially the same synthetic procedure as in Synthetic Preparation 1 described above excepting replacement of 117.2 g of the 3-acryloxypropyl trimethoxy silane with 56.1 g (0.50 mole) of allyl acrylate.

SYNTHETIC PREPARATION 5 (COMPARATIVE)

Into a flask of 300 ml capacity equipped with a stirrer and a thermometer were introduced 87.4 g (0.37 mole) of 3-glycidyloxypropyl trimethoxy silane, 30.5 g (0.17 mole) of 3-aminopropyl trimethoxy silane and 120.7 g (0.79 mole) of tetramethoxy silane and the mixture was agitated for 4 hours at 110° to 120° C. to effect the reaction. The reaction mixture was then subjected to stripping at 110° to 120° C. under a reduced pressure of 5 mmHg and freed from the unreacted tetramethoxy silane to give 82.0 g of a liquid product, referred to as C-V hereinbelow, which could be identified from the results of the analyses to be a compound expressed by the structural formula

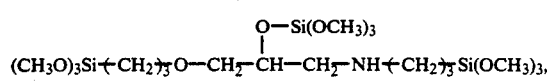

(CH$_3$O)$_3$Si—(CH$_2$)$_3$—O—CH$_2$—CH(—O—Si(OCH$_3$)$_3$)—CH$_2$—NH—(CH$_2$)$_3$—Si(OCH$_3$)$_3$, taught to be useful as an adhesion improver in Japanese Patent Publications 52-8854 and 55-41702. The above mentioned yield of the product corresponds to 90% of the theoretical value.

EXAMPLE 1

Five adhesive compositions, referred to as the Compositions I to V hereinbelow, were prepared each by uniformly blending 100 parts of a dimethyl polysiloxane having a viscosity of 10000 centipoise at 25° C. and terminated at each molecular chain end with a dimethyl vinyl silyl group, of which the content of vinyl groups was 0.00525 mole per 100 g, with 4.0 parts of a methyl hydrogen polysiloxane containing 0.0069 mole of silicon-bonded hydrogen atoms per 100 g expressed by the average structural formula

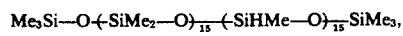

Me$_3$Si—O—(SiMe$_2$—O)$_{15}$—(SiHMe—O)$_{15}$—SiMe$_3$, in which Me is a methyl group, 1.0 part of the compound C-I, C-II, C-III, C-IV or C-V, respectively, obtained in the above described Synthetic Preparations 1 to 5, 0.05 part of an isopropyl alcohol solution containing 2% by weight as platinum of chloroplatinic acid and 25 parts of a finely divided silica filler after a hydrophobilizing treatment having a specific surface area of 170 m$^2$/g as determined by the BET method.

Each of these Compositions I to V was applied to the surface of test panels of a polycarbonate resin and cured by keeping for 1 hour at a temperature of 80° C., 100° C. or 120° C. or for 96 hours at 20° C. followed by the determination of the shearing adhesive bonding strength according to the procedure specified in JIS K 6850 to give the results shown in Table 1 below in kgf/cm$^2$.

TABLE 1

| Curing temperature, °C. | Curing time, hours | Composition No. | | | | |
|---|---|---|---|---|---|---|
| | | I | II | II | IV | V |
| 80 | 1 | 26 | 20 | 15 | 21 | 12 |
| 100 | 1 | 26 | 22 | 16 | 21 | 17 |
| 120 | 1 | 27 | 23 | 22 | 22 | 20 |
| 20 | 96 | 23 | 19 | 14 | 20 | 10 |

Separately, the same tests for the shearing adhesive bonding strength as above were conducted by replacing the polycarbonate test panels with test panels of glass, aluminum, nickel, mild steel or iron, in which curing of the adhesive compositions was effected at 120° C. for 1 hour, to give the results shown in Table 2 below in kgf/cm$^2$.

TABLE 2

| Test panels | Composition No. | | | | |
|---|---|---|---|---|---|
| | I | II | III | IV | V |
| Glass | 29 | 28 | 25 | 28 | 23 |
| Aluminum | 29 | 27 | 25 | 29 | 23 |
| Nickel | 28 | 24 | 23 | 26 | 18 |
| Mild steel | 29 | 27 | 24 | 28 | 20 |
| Iron | 29 | 27 | 23 | 28 | 21 |

EXAMPLE 2

The compounds C-I to C-V prepared in Synthetic Preparations 1 to 5 were each kept at 40° C. for three months under a hermetically sealed condition and five adhesive compositions, referred to as the Compositions Ia, IIa, IIIa, IVa and Va, respectively, hereinbelow, were prepared each in the same formulation as for the Compositions I to V in Example 1 using the compounds C-I to C-V after the 3-month aging.

These adhesive Compositions Ia to Va were subjected to the tests of shearing adhesive bonding strength in the same manner as in Example 1 by curing at 80° C. or 100° C. for 1 hour to give the results shown in Table 3 below in kgf/cm².

TABLE 3

| Curing temperature, °C. | Composition No. | | | | |
|---|---|---|---|---|---|
| | Ia | IIa | IIIa | IVa | Va |
| 80 | 25 | 18 | 14 | 20 | 0 |
| 100 | 27 | 22 | 15 | 22 | 5 |

What is claimed is:

1. An adhesive organopolysiloxane composition which comprises, as a mixture:
   (a) 100 parts by weight of a diorganopolysiloxane having, in a molecule, at least two alkenyl groups bonded to the silicon atoms;
   (b) an organohydrogenpolysiloxane having, in a molecule, at least three hydrogen atoms directly bonded to the silicon atoms in such an amount that from 0.5 to 10 moles of the silicon-bonded hydrogen atoms are provided per mole of the alkenyl groups in the component (a);
   (c) from 0.01 to 10 parts by weight of -aminopropionyl-containing compound represented by the general formula $$X-NR-CH_2-CHR-CO-Y-X,$$

in which each R is, independently from the other, a hydrogen atom or a monovalent hydrocarbon group having 1 to 10 carbon atoms, Y is an oxygen atom or a group of the formula NR and each X is, independently from the other, a monovalent hydrocarbon group having 1 to 10 carbon atoms or an organosilyl-substituted monovalent hydrocarbon group of the formula $Z_3SiQ$, Z being, each independently from the others, a monovalent hydrocarbon group or an alkoxy group having 1 to 8 carbon atoms and Q being a divalent hydrocarbon group, containing one or a plurality of methylene groups $-CH_2-$ one of which may be replaced with an imino group $-NH-$ with the proviso that at least either one of the two X groups is an organosilyl-substituted monovalent hydrocarbon group of the formula $Z_3SiQ$ of which at least one of the three Z groups is an alkoxy group or an alkoxy-substituted alkoxy group; and
   (d) a compound of a platinum-group metal in a catalytic amount.

2. The adhesive organopolysiloxane composition as claimed in claim 1 in which the alkenyl group in the diorganopolysiloxane as the component (a) is a vinyl group.

3. The adhesive organopolysiloxane composition as claimed in claim 1 in which the organic groups in the diorganopolysiloxane as the component (a) other than the alkenyl groups are methyl groups.

4. The adhesive organopolysiloxane composition as claimed in claim 1 in which the diorganopolysiloxane as the component (a) has a viscosity in the range from 50 to 300,000 centipoise at 25° C.

5. The adhesive organopolysiloxane composition as claimed in claim 1 in which the organohydrogenpolysiloxane as the component (b) has a viscosity in the range from 0.9 to 10,000 centipoise at 25° C.

6. The adhesive organopolysiloxane composition as claimed in claim 1 in which the β-aminopropionyl-containing compound as the component (c) is selected from the group consisting of the compounds expressed by the structural formulas of:

$$(CH_3O)_3Si-(CH_2)_3-NH-(CH_2)_2-CO-O-(CH_2)_3-Si(OCH_3)_3;$$

$$C_6H_5-CH_2-NH-(CH_2)_2-CO-O-(CH_2)_3-Si(OCH_3)_3;$$

$$CH_2=CH-CH_2-NH-(CH_2)_2-CO-O-(CH_2)_3-Si(OCH_3)_3;$$

and $$(CH_3O)_3Si-(CH_2)_3-NH-(CH_2)_2-CO-O-CH_2-CH=CH_2.$$

7. The adhesive organopolysiloxane composition as claimed in claim 1 in which the compound of a platinum-group metal as the component (d) is a compound of platinum.

8. The adhesive organopolysiloxane composition as claimed in claim 1 in which the amount of the compound of a platinum-group metal as the component (d) is in the range from 0.1 to 1000 ppm by weight calculated as metal based on the total amount of the components (a) and (b).

9. An article consisting of at least two parts adhesively bonded with the adhesive organopolysiloxane composition according to claim 1 in a cured state.

* * * * *